United States Patent
Sykaluk

[11] Patent Number: 6,039,871
[45] Date of Patent: Mar. 21, 2000

[54] SMALL DIALYSIS DEVICE

[75] Inventor: Laura L. Sykaluk, Rockford, Ill.

[73] Assignee: Pierce Chemical Company, Rockford, Ill.

[21] Appl. No.: 09/161,328

[22] Filed: Sep. 25, 1998

[51] Int. Cl.⁷ ................................................ B01D 63/00
[52] U.S. Cl. .............................. 210/321.71; 210/500.29; 210/321.75; 210/445; 210/446; 210/476; 210/477
[58] Field of Search ........................... 210/321.6, 321.71, 210/321.75, 500.29, 500.36, 439, 445, 476, 477, 232, 446

[56] References Cited

U.S. PATENT DOCUMENTS

| | | |
|---|---|---|
| 567,387 | 9/1896 | Hawley . |
| 789,062 | 5/1905 | Prescott . |
| 863,813 | 8/1907 | Tyler . |
| 4,450,076 | 5/1984 | Medicus et al. ............... 210/242.1 |
| 4,988,437 | 1/1991 | Gefter et al. ................... 210/445 |
| 5,015,398 | 5/1991 | Cocuzzi ........................ 210/476 |

Primary Examiner—Robert J. Popovics

[57] ABSTRACT

In accordance with the present invention, there is provided an improved device for the dialysis of small fluid samples, particularly biological fluids. The device of the present invention contains a cylindrical outer sleeve open at both ends. The sidewall portion of the sleeve near the top end contains a channel in and around the inner surface and the sidewall continues to extend upwardly from the channel to the open top end. An inner sleeve is positioned within and in axial alignment with the outer sleeve. The inner sleeve has a cylindrical flange at an open top end that is inserted in the channel of the outer sleeve. The bottom end of the inner sleeve is open and extends below the bottom end of the outer sleeve. A space exists between the sidewalls of the two sleeves near the bottom end of the outer sleeve. A dialysis membrane covers the open bottom end of the inner sleeve. The membrane extends upwardly and around the sidewall of the sleeve and fills the space between the sidewalls of the sleeves near the bottom end of the outer sleeve so that the sleeves are in an airtight relationship in this region.

6 Claims, 1 Drawing Sheet

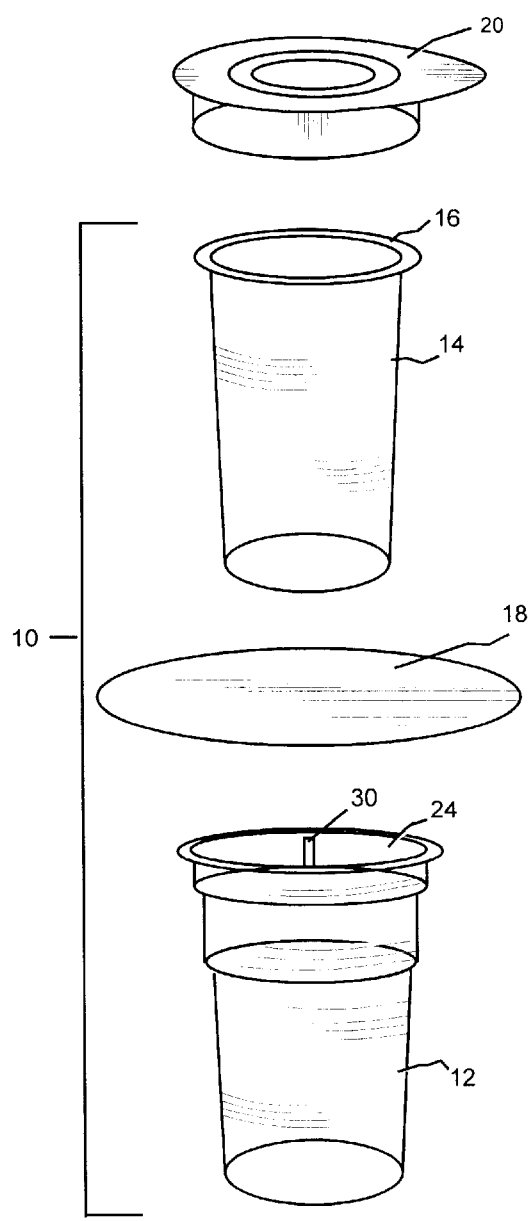
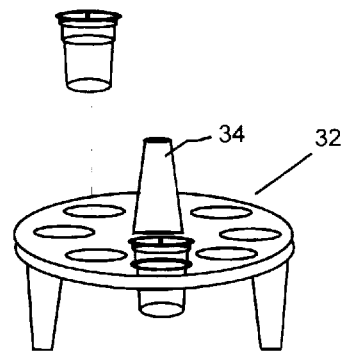
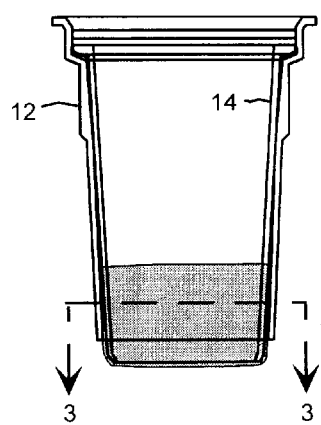
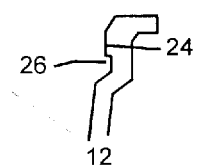
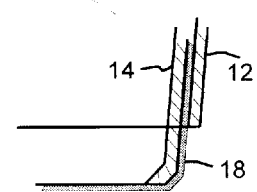
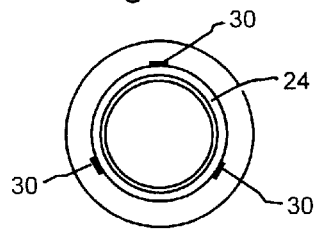
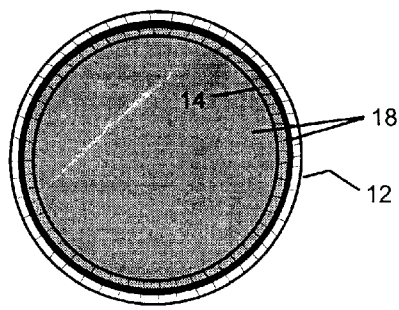

SMALL DIALYSIS DEVICE

FIELD OF INVENTION

The present invention relates to the dialysis of fluids and, more particularly, to a disposable device useful for accomplishing the dialysis of small fluid samples.

BACKGROUND OF INVENTION

Advanced analytical techniques requiring small sample sizes and the expense and scarcity of many biologically active materials have created a demand in analytical and research applications for small-scale dialysis equipment and procedures. It is not uncommon that dialysis may be required on fluid samples of less than 500 microliters and frequently less than 150 microliters, such as on the order of 10–100 microliters. Some special problems encountered in dialyzing small samples center on difficulty in handling the sample, loss of sample, and achieving effective dialysis.

Horowitz and Barnes (Analytical Biochemistry, 128, 478–480, 1993, entitled "A Simple, Inexpensive, and Precise Microcell For the Exchange Dialysis and Equilibrium Dialysis of Small Samples") describe a device for dialyzing small samples (10–300 microliters). This device is constructed from commonly available 1.5 ml microcentrifuge tubes using a scalpel to cut a ring from the latter. The sample is loaded into the lid of the tube, the dialysis membrane is placed on top, and the ring is closed over the membrane. Preparation and use of the device is time consuming and awkward, sample recovery is difficult, and dialysis is not always achieved due to sample leakage.

SUMMARY OF THE INVENTION

In accordance with the present invention, there is provided an improved device for the dialysis of small fluid samples, particularly biological fluids. The device is simple to use, allowing for the easy addition and removal of sample. Furthermore, use of the device achieves very efficient dialysis of the fluid sample.

The device of the present invention contains a cylindrical outer sleeve open at both ends. The sidewall portion of the sleeve near the top end contains a channel in and around the inner surface and the sidewall continues to extend upwardly from the channel to the open top end. An inner sleeve is positioned within and in axial alignment with the outer sleeve. The inner sleeve has a cylindrical flange at an open top end which is inserted in the channel of the outer sleeve. The bottom end of the inner sleeve is open and extends below the bottom end of the outer sleeve. A space exists between the sidewalls of the two sleeves near the bottom end of the outer sleeve. A dialysis membrane covers the open bottom end of the inner sleeve. The membrane extends upwardly and around the sidewall of the sleeve and fills the space between the sidewalls of the sleeves near the bottom end of the outer sleeve so that the sleeves are in an air tight relationship in this region.

The device of the present invention can be assembled by first wrapping a dialysis membrane over the bottom end of the inner sleeve or, alternatively, placing the membrane over the top of the outer sleeve. For thin membranes, e.g., less than about 1 mil, this membrane can be assembled in a dry state. For thicker membranes wetted (misted) membranes with water or dilute glycerol are most useful. The inner sleeve is then pushed into the outer sleeve until the flanged, top end of the inner sleeve engages the channel in the outer sleeve and snaps into the channel. To confirm that the membrane is sealed properly in air tight relationship between the sleeves at the bottom and that there are no channels, a vacuum or air pressure can be applied. The presence of channels is evidenced by a loss of back pressure retention, as measured against a standard.

In accordance with a preferred aspect of the present invention, that portion of the sidewall of the inner sleeve extending below the bottom end of the outer sleeve, is chamfered, i.e. contains a radius or bevel. This assists in assembly of the device by minimizing the possibility of tearing or rupturing of the membrane as the inner sleeve is inserted through the outer sleeve. A further preferred aspect resides in providing at least one groove positioned lengthwise in the inner surface of the sidewall of the outer sleeve above the channel. At its lower end, the groove intersects the channel and provides an added degree of flexibility in the sidewall which assists in achieving a snap fit of the flange into the channel. Preferably, there are several, e.g., three, such grooves equally spaced around the inner surface of the sidewall.

BRIEF DESCRIPTION OF THE DRAWINGS

FIG. 1 is an exploded perspective view showing, in disassembled relationship, the device of this invention.

FIG. 2 is a cross-sectional side view of the device in assembled form.

FIG. 3 is a cross-sectional view taken along line 3—3 of FIG. 2.

FIG. 4 is a top view of the outer sleeve shown in FIG. 1.

FIG. 5 is an exploded, fragmented view of the outer sleeve sidewall portion shown in FIG. 2.

FIG. 6 is an exploded, fragmented view illustrating the chamfer at the bottom of the inner tube.

FIG. 7 is a perspective view of a flotation device useful in accomplishing dialysis using the device of this invention.

DETAILED DESCRIPTION OF THE INVENTION

Turning to the drawings, FIG. 1 illustrates a dialysis device 10 according to the present invention depicting the elements thereof in disassembled relationship. The device 10 includes a cylindrical outer sleeve 12 open at both the top and bottom ends and a cylindrical inner sleeve 14 having an open bottom end and an open top end terminating in a cylindrical flange 16. As shown, a dialysis membrane 18 is disposed between the two sleeves. Having the top end of both sleeves and, in turn, the top end of the device open allows for easy fluid sample addition or removal during dialysis. It also permits use of a standard laboratory pipette. As opposed to use of a needle, which is practiced with some other dialysis devices, a pipette permits dialysis of more viscous samples and avoids sample damage such as shearing which might occur with DNA samples. As also illustrated in FIG. 1, a cap 20 adapted to fit into the open end of the outer sleeve 12 may also be provided along with the basic device illustrated herein.

As shown in FIG. 2, as assembled, the bottom 22 of the inner sleeve 14 extends below the bottom of the outer sleeve 12 and is covered by the membrane 18. By positioning the membrane surface through which dialysis occurs below the bottom of the outer sleeve, trapping of air during dialysis between the membrane and the dialysate is avoided.

As further illustrated in the drawings, the membrane 18 extends upwardly around the sidewall of the inner sleeve 14 and fills the space between the sidewalls of the two sleeves in the region adjacent the bottom of the outer sleeve. In this fashion, the sleeves are secured in an air tight relationship in this region and channels between the sleeves, which can result in undesirable wicking of sample or dialysate, are eliminated. To accomplish a tight fit, the drafts (tapers) of the inner and outer sleeves in the region adjacent the bottom of the outer sleeve are matching and the thickness of the membrane is slightly greater than the space between the sidewalls of the sleeves. For a dialysis device having a length of about 1.7 cm and an outer sleeve diameter at the bottom of about 0.6 cm, an air tight fit over a length from the outer sleeve bottom of at least 2 mm up the sidewall of the sleeves is desirable. Preferably, the air tight fit extends up the length of the sidewalls to the end of the membrane.

Turning again to the drawings and particularly FIG. 5, the sidewall portion 24 of the outer sleeve 12 near the top end contains a channel 26 in and around its inner surface. As assembled, the cylindrical flange 16 forming the top of the inner sleeve is inserted in the channel 26. To this end, the outer diameter of the flange is slightly greater than the inner diameter of the sidewall of the outer sleeve which extends above the channel. Since once the flange snaps into the channel, the position of the sleeves relative to each other is fixed, the location of the channel in the sidewall is determined such that, as above discussed, the bottom of the inner sleeve covered by the membrane extends below the bottom of the outer sleeve.

In a preferred embodiment as shown in FIGS. 1 and 4, the inner surface of the sidewall portion above the channel contains three longitudinally extending grooves 30, the bottom of which intersect the channel 26. These grooves enhance the flexibility of the sidewall and assist in achieving insertion of the flange 16 into the channel 26. As shown, the grooves are equally spaced around the inner surface of the sidewall 24.

A further preferred embodiment is particularly illustrated in FIGS. 2 and 6. As shown, the bottom 32 of the inner sleeve 14 which, in assembled relationship, extends beyond the bottom of the outer sleeve is chamfered or beveled. In this fashion, damage to the membrane in the form of tear of rupture during assembly of the device can be minimized.

Conventional materials can be used for the preparation of the device of this invention. Regenerated cellulose is a useful dialysis membrane material while a plastic material, such as polypropylene which is flexible, is useful in fabricating the sleeves. Both of these materials are low protein absorbing substances and survive common sterilization procedures well.

FIG. 7 illustrates a manner in which the devices of this invention can be used to accomplish dialysis of a sample or simultaneously accomplish dialysis of multiple samples. A floatation device 32 containing a handle 34 is used. The lower end of the dialysis device containing the membrane extends through the openings in the float and into the dialysate.

I claim:

1. A device useful for the dialysis of small samples of fluids comprising:

a cylindrical outer sleeve having an open top end and an open bottom end, the sidewall portion of the sleeve near the top end containing a channel in and around the inner surface with said sidewall extending upwardly from said channel toward said open top end;

a cylindrical inner sleeve having an open, flanged top end and an open bottom end, said inner sleeve being positioned within and in axial alignment with said outer sleeve with the flange being inserted in the channel of the outer sleeve and the sidewall adjacent to the bottom end of the inner sleeve extending below the bottom end of the outer sleeve, there being a space between the sidewalls of the sleeves in the region adjacent to the bottom end of the outer sleeve; and a dialysis membrane covering the open, bottom end of the inner sleeve and extending upwardly and around the sidewall of the said sleeve so as to fill said space between the sidewalls of the two sleeves and secure the sleeves in an air tight relationship in said region.

2. The device of claim 1 wherein the sidewall of the inner sleeve extending below the bottom end of the outer sleeve is chamfered to assist in assembly of the device without tear or rupture of the membrane.

3. The device of claim 1 wherein the inner surface of the sidewall of the outer sleeve extending above the channel contains at least one groove positioned lengthwise therein to enhance the flexibility of the outer sleeve and assist in the insertion of the flange into the channel.

4. The device of claim 3 containing three of said grooves equally spaced around said sidewall.

5. The device of claim 4 wherein the sidewall of the inner sleeve extending below the bottom end of the outer sleeve is chamfered to assist in assembly of the device without tear or rupture of the membrane.

6. The device of claim 5 wherein the sleeves are polypropylene and the membrane is regenerated cellulose.

\* \* \* \* \*